US005821074A

United States Patent [19]

Wong et al.

[11] Patent Number: 5,821,074
[45] Date of Patent: *Oct. 13, 1998

[54] METHOD AND COMPOSITIONS FOR ENHANCING AMINOLEVULINIC ACID DEHYDRATASE ASSAY

[75] Inventors: Martin Wong, Grayslake; David M. Finley, Spring Grove, both of Ill.

[73] Assignee: Abbott Laboratories, Abbott Park, Ill.

[*] Notice: The term of this patent shall not extend beyond the expiration date of Pat. No. 5,597,702.

[21] Appl. No.: 507,168

[22] Filed: Jul. 26, 1995

Related U.S. Application Data

[63] Continuation of Ser. No. 171,121, Dec. 21, 1993, abandoned.

[51] Int. Cl.$^6$ .............................. C12Q 1/34; G01N 33/00
[52] U.S. Cl. ................... 435/18; 435/4; 435/268; 435/810; 435/962; 435/963; 436/63; 436/73; 436/74; 436/76; 514/836
[58] Field of Search .................................. 435/18, 4, 268, 435/810, 962, 963; 436/63, 73, 74, 76; 514/836

[56] References Cited

U.S. PATENT DOCUMENTS

| | | | |
|---|---|---|---|
| 4,042,329 | 8/1977 | Hochstrasser | 23/230 B |
| 4,203,971 | 5/1980 | Buchanan | 424/92 |
| 4,912,035 | 3/1990 | Belly et al. | 435/29 |
| 5,112,749 | 5/1992 | Brey, III et al. | 435/172.3 |
| 5,151,412 | 9/1992 | Brown | 514/8 |
| 5,354,652 | 10/1994 | Silbergeld | 435/4 |
| 5,368,707 | 11/1994 | Henkens et al. | 204/153.12 |

FOREIGN PATENT DOCUMENTS

WO93/01310  1/1993  WIPO.

OTHER PUBLICATIONS

Odgen et al, *Methods in Enzymology*, vol. 152, p. 65, 1987.
Joffe et al, *Biological Trace Element Research*, vol. 28, No. 3, pp. 223–231, Mar. 1991.
Silbergeld, *Chemical Abstracts*, vol. 118, p. 345, Ref. #185700z, 1993 (PCT Int. App. WO 9301310, 21 Jan. 1993).
Cavallerr et al, *Chemical Abstracts*, vol. 88, pp. 385–386, Ref. #1764324, 1978 (Br. J. Ind. Med. 1978, 351), 21–6.
Despaux–Rogers et al, *Chemical Abstracts*, vol. 105, p. 298, Ref. #37935w (Int. Arch. Occup. Enviorn. Health 1986, 57(4) 303–13).
A. Berlin, et al., European Standarized Method for the Determination of δ–Aminolevulinic Acid Dehydratase Activity in Blood, *Z. Klin. Chem. Klin. Biochem.* S. 389–390 (1974).
P. N. B. Gibbs, et al., Purification and properties of 5–aminolaevulinate dehydratase from human erythrocytes, *Biochem. J.*, 230, 25–34 (1985).
S. Sassa, Delta–Aminolevulinic Acid Dehydratase Assay, *Enzyme* 28, 133–145 (1982).
P. M. Anderson, et al., Purification and Properties of δ–Aminolevulinate Dehydrase from Human Erythrocytes, *The Journal of Biological Chemistry*, vol. 254, No. 15, Issue of Aug. 10, 6924–6930 (1979).
M. T. Volosin, et al., Use of the Carbon Rod Atomizer for Analysis of Lead in Blood: Three Methods Compared, *Clinical Chemistry*, vol. 21, No. 13, 1986–1987 (1975).
J. O. Pierce, et al., Lead, Chromium, and Molybdenum by Atomic Absorption, *Arch Environ Health*, vol. 13, 208–212 (Aug. 1966).

*Primary Examiner*—Howard E. Schain
*Assistant Examiner*—Abdel A. Mohamed
*Attorney, Agent, or Firm*—David L. Weinstein

[57] ABSTRACT

The present invention provides a method of improving the sensitivity and accuracy of a lead assay. The method enhances the recovery of lead during isolation of the lead from interfering compounds by maintaining the lead in a sample solution and making the recovered lead available for detection by the assay. An enhancing reagent complexes with the lead isolated in the sample solution. The enhancer includes a chelator having a lead equilibrium binding constant in the range of about 4 log K to about 13 log K. A kit for performing such a lead assay is also provided.

28 Claims, No Drawings

METHOD AND COMPOSITIONS FOR ENHANCING AMINOLEVULINIC ACID DEHYDRATASE ASSAY

This application is a continuation of application Ser. No. 08/171,121, filed Dec. 21, 1993 now abandoned.

RELATED APPLICATION

Related U.S. application Ser. No. 08/171,035 filed on even date herewith now abandoned discloses certain reagents which are suitable for use in the present application. The entire teaching and disclosure of that co-pending application is incorporated herein by reference.

FIELD OF THE INVENTION

The present invention relates to assays for detecting metal ions such as lead and, more particularly, utilizing selected chelators to enhance the sensitivity and accuracy of a whole blood lead assay using aminolevulinic acid dehydratase.

BACKGROUND OF THE INVENTION

The rapid determination of trace metals in biological and environmental systems is increasingly important in identifying potential hazards and preserving the public health. The toxicity of certain metals such as lead is well-known. The absorption of even trace amounts of lead can cause severe damage to human organs. The numerous and widespread sources of lead in the environment, including the food supply, compounds the problems of screening affected groups.

It is generally recognized that lead poisoning occurs in children at blood levels as low as 10–15 ug/dl. Lead contamination of environmental sources such as water, dust and soil require identification at even lower levels. To measure these amounts, the analytical techniques must be sensitive, contaminant-specific, and reliable.

An early technique for identifying trace metals in biologic systems is described by J. Pierce et al., "Lead, Chromium, and Molybdenum by Atomic Absorption, *Arch. Environ. Health,* 13:209 (1966). This measurement technique requires extraction of the lead from blood samples by precipitating the blood proteins with trichloroacetic acid and complexing the lead with a chelator under acidic conditions. The metal complex was then analyzed by atomic absorption. The skill and expensive instrumentation required by this technique limits its applicability for detecting lead contamination.

The use of d-aminolevulinic acid dehydratase (ALAD) activity in red blood cells to determine exposure to environmental lead is described by A. Berlin, et al., "European Standardized Method for the Determination of d-Aminolevulinic Acid Dehydratase Activity in Blood," *Z. Klin. Chem. Klin. Biochem.,* 12 Jg. 1974, S. 389–390. The assay entails incubation of the enzyme with excess d-aminolevulinic acid (ALA). The porphobilinogen (PBG) which is formed within a fixed time is mixed with modified Ehrlich's reagent, and the color developed is measured photometrically against a blank. The quantity of PBG produced is a measurement of the ALAD activity and corresponds to the low levels of lead exposure.

A method of colormetric determination of ALAD is presented by S. Sassa, "Delta-Aminolevulinic Acid Dehydratase Assay," *Enzyme,* 28:133–145 (1982). The effect of reducing agents like dithiothreitol (DTT) on the enzyme activity and its use for the detection of subclinical lead poisoning by assaying the enzyme activity in erythrocytes is disclosed.

Two articles, each entitled "Purification and Properties of d-Aminolevulinate Dehydrase from Human Erythrocytes," first published by P. Anderson, et al., *J. Biol. Chem.,* 254:6924–6930 (1979) and subsequently by P. Gibbs, et al., *Biochem J.,* 230:25–34 (1985), disclose assays demonstrating lead as a noncompetitive inhibitor of ALAD activity. The incubation mixtures contained DTT, ALAD and ALA in a buffer solution. The incubations were terminated by the addition of TCA containing $HgCl_2$. The solution was centrifuged and the supernatant was added to modified Ehrlich's reagent in acetic acid and $HClO_4$. The colored complex formed with PBG was measured spectrophotometrically.

A similar assay measuring the activity of ALAD after exposure to lead containing samples is disclosed in a published PCT application WO 93/01310 to Silbergeld. The application suggests utilizing other well-know methods like conjugating or attaching a label to either the substrate or product and quantifying the amount of labeled material present after a defined reaction period. Another approach suggested uses a known antibody that binds specifically to unoccupied lead binding sites of ALAD.

A significant problem in using an ALAD assay is the poor lead recovery in the preparation of a sample. For an ALAD assay a sample of whole blood is typically pretreated with acid to release lead from the red blood cells and to precipitate sample proteins. The pretreated sample is then neutralized before the enzyme is added for incubation. Usually, the recovery of lead is less than the lead-spiked water control sample.

Effective screening of potentially affected people or sources demands an analytical technique which is conveniently used, inexpensive and convenient both as to the sample size and administration of the test. For early detection, contamination prevention, or corrective treatment, the time interval between sampling and results is preferably minimal. Although the lead assay using the enzyme ALAD has proven useful, there is a need to enhance the sensitivity and accuracy. The present invention provides enhancing reagents and methods which improve the sensitivity of the assay by recovering more of the lead in the sample during pretreatment and neutralization makes it available to inhibit the activity of the ALAD enzyme.

SUMMARY OF THE INVENTION

The present invention provides a method of improving the sensitivity and accuracy of a lead assay. The method enhances the recovery of lead during isolation of the lead from interfering compounds by maintaining the lead in a sample solution and making the recovered lead available for detection by the assay.

The method includes isolating the lead in a sample solution from compounds which interfere with the lead assay. The recovery of the lead is enhanced in the sample solution and the lead is made available for assay. An ALAD enzyme is incubated in the sample solution in the presence of a substrate. The enzyme incubation step is stopped after a predetermined time interval. The extent of the enzyme activity is subsequently photometrically determined.

The present invention also provides an enhancing reagent for enhancing the recovery of lead in a test sample and making the lead available to improve the sensitivity and accuracy of a lead assay. The enhancer comprises a chelator having a lead equilibrium binding constant in the range of about 4 log K to about 13 log K. A kit for performing such a lead assay is also provided.

Accordingly, it is an advantage of the present invention to provide a more sensitive and accurate lead assay using the ALAD enzyme.

Another advantage of the present invention is to provide a method of recovering more lead after isolation of the lead in a sample and make it available for detection in an assay.

A further advantage of the present invention is to provide an enhancer reagent which has a minimal adverse effect on the other steps of the assay.

Other and further advantages, embodiments, variations and the like will be apparent to those skilled in the art from the present specification taken with the accompanying drawings and appended claims.

DETAILED DESCRIPTION

The present invention relates to the enhancement of the sensitivity of an assay for determining lead by exposing an ALAD enzyme to a sample such as whole blood and measuring the inhibition of activity. Preparation for the assay includes pretreating the sample to expose and recover the lead from within the red blood cells and to precipitate interfering compounds such as proteins, endogenous ALAD, PBG, ALA and the like. Acid is commonly used to pretreat the sample. The interfering compounds are then pelleted by centrifugation leaving a supernatant which contains the lead isolated from the interfering compounds.

The acidified supernatant containing the recovered lead is then separated for additional processing. The supernatant must be neutralized prior to incubation of the ALAD enzyme. A neutralizing reagent is added to bring the supernatant sample to a neutral pH. During this neutralization step, it is important to maintain the lead present in the supernatant sample in an enzyme accessible form which enhances the sensitivity and accuracy of the assay by increasing the amount of lead which is recovered from the sample and available for enzyme detection.

The present invention improves the recovery of lead from the sample by adding an enhancing reagent which keeps the lead in the supernatant sample during the neutralization step. The enhancer forms a complex or compound with the lead released in the supernatant sample. The enhancer-lead complex maintains the lead in the supernatant sample and avoids its loss due to precipitation or the like. The enhancer must then make the lead available for inhibiting the activity of the ALAD enzyme. The enhancer reagent also must avoid or minimize any interference, directly or indirectly, with the activity of the ALAD enzyme. Indirect interference, for example, results from affecting the concentration of zinc in the assay. Having the enhancer reagent form a complex with zinc decreases the activity of the ALAD enzyme.

As used herein, the term "enhancer" means a reagent provided by the present invention that increases the accuracy and sensitivity of a lead assay in comparison to that achieved by the assay in the absence of the reagent. The enhancer forms a complex or compound with the released lead, maintains availability of the lead in the sample and then allows it to inhibit the ALAD enzyme activity. The term "neutralizing reagent" is the solution which brings the acidified supernatant sample to a neutral pH.

The present invention has found that certain chelating reagents complex with the sample lead and still make it available to inhibit the activity of the ALAD enzyme. The currently preferred enhancers for use with the present invention are N-benzyliminodiacetic acid (BenzylIDA), L-histidine monohydrochloride monohydrate (Histidine), N-(2-hydroxyethyl)-iminodiacetic acid (HEIDA), iminodiacetic acid (IDA), DL-penicillamine (PEN), methyliminodiacetic acid (MIDA), nitrilotriacetic acid (NTA), sodium citrate, and d-hydroxyquinoline-5-sulfonic acid hydrate (HQSA).

The present invention has also found that enhancers which exhibit a characteristic to form a complex with $Pb^{+2}$ as described by the $Pb^{+2}$ equilibrium binding constant (K) in the range of about 4 log K to about 13 log K are suitable enhancers. Preferably, the enhancer exhibits a $Pb^{+2}$ equilibrium binding constant in the range of about 6 log K to about 9 log K.

All the of preferred enhancers identified above have a $Pb^{+2}$ equilibrium binding constant within the suitable range. Other enhancers which similarly exhibit a suitable $Pb^{+2}$ equilibrium binding constant include 8-hydroxy-5-(2'-hydroxyphenylazo) quinoline, 8-hydroxy-5-(phenylazo) quinoline, N-(2-carboxyphenyl)iminodiacetic acid, N-(acetonyl)iminodiacetic acid, N-(dithiocarboxy) aminoacetic acid, N,N-bis(2'-hydroxyethyl)glycine, and glycine.

Other enhancers contemplated by the present invention include dihydroxyphenyl acetic acid, N-(2'carboxyethyl) iminodiacetic acid, dihydroxybenzoic acid, 3,4, dihydroxybenzene sulfonic acid, melonic acid, 1-hydroxy-1-(3'-pyridyl) methane sulfonic acid, and 4-aminopyridine-2,6-dicarboxylic acid.

The present invention contemplates a method of enhancing the sensitivity and accuracy of a lead assay by isolating the lead in a sample solution from compounds which interfere with the lead assay. The pretreatment of the sample can be accomplished with conventional techniques such as by adding TCA, nitric acid, 5-sulfosalicylic acid, or perchloric acid to the whole blood sample.

The acidified sample must then be neutralized before the assay can continue with incubation of the ALAD enzyme in its presence. To prevent precipitation of the lead or the formation of a lead complex which is not detectable by the assay, the enhancer is present in the sample during adjustment of the sample's pH to neutral. The enhancer recovers the lead in the sample solution and makes the lead available for continuing the assay.

The assay continues by incubating an ALAD enzyme in the sample solution in the presence of a substrate such as ALA. The enzyme incubation step is stopped after a predetermined time interval. The product of the enzyme activity is PBG. By reacting the PBG with Erhlich's reagent to form a chromophore, one can photometrically determine the extent of the enzyme activity. Other coloring reagents containing dimethylaminobenzaldehyde, dimethylaminocinnamaldehyde or their derivatives are suitable for use with the present invention.

The following Examples are set forth for the purposes of illustration and should not be construed as limiting.

EXAMPLES

Materials

All the reagents used in the present invention are available commercially. The aminolevulinic acid (ALA) and d-aminolevulinic acid dehydratase (ALAD) were both purchased from Sigma Company of St Louis, Mo., as cat. nos. A-3785 and A-0644, respectively. The $HgCl_2$, dimethylaminobenzaldehyde (DMAB) and dithiothreitol are also available from Sigma as cat. nos. M-6529, D-8904 and D-0632. The buffer (bis[2-hydroxyethyl]imino-tris[hydroxymethyl] methane (BisTris), concentrated $HNO_3$ acid, NaOH pellets, $ZnCl_2$ (99+% pure), and trichloroacetic acid (TCA) are available from Aldrich Chemical Company of Milwaukee, Wis., as cat. nos. 15,666-3, 22,571-1, 30,657-6, 22,999-7, and 25,139-9. The 10 mg/dl lead standard was also purchased from Aldrich as cat. no. 31,903-3. The glacial acetic acid and 60% perchloric acid were purchased from Fisher as cat. nos. A38-212 and A228-1

The enhancers tested include: N-benzyliminodiacetic acid (BenzylIDA) purchased from Aldrich as cat. no. B2,475-8 (98% pure); ethylenebis (oxyethylenenitrilo)tetraacetic acid (EGTA) Aldrich cat. no. 23,453-2 (97% pure); ethylenediaminetetraacetic acid (EDTA) purchased from Sigma cat. no. ED2P (98% pure); L-histidine monohydrochloride monohydrate (Histidine) purchased as Aldrich cat. no. H1,520-9 (98% pure); N-(2-hydroxyethyl)-iminodiacetic acid (HEIDA) purchased as Aldrich cat no. 15,814-3 (98% pure); Iminodiacetic Acid (IDA) purchased from Aldrich cat. no. I-120-0 (97% pure); DL-penicillamine (PEN) purchased from Aldrich cat. no. P60-8 (99+% pure); methyliminodiacetic acid (MIDA) purchased from Aldrich cat. no. M5,100-8 (99% pure); nitrilotriacetic acid (NTA) purchased from Aldrich cat no. 10,629-1 (99+% pure); sodium citrate purchased from Mallinckrodt cat. no. 0754 (99.7% pure); d-hydroxyquinoline-5-sulfonic acid hydrate (HQSA) purchased from Aldrich cat. no. H5,875-7 (98% pure).

The spectrophotometer used for absorbance measurements was a LKB Ultraspec II Model 4050.

Method

All flasks used in the preparation of solutions described herein were washed with 1 N $HNO_3$. The solutions prepared were stored at room temperature unless otherwise noted. The pH of 50 ml of HPLC grade distilled water was adjusted to a pH 1.50 by adding an appropriate amount of concentrated $HNO_3$. A 20 mM $ZnCl_2$ solution was prepared by adding pH 1.50 distilled water to 0.0340 g. $ZnCl_2$ for a final solution weight of 12.500 g. The solution was then thoroughly mixed.

A solution of 200 ml 1.5 M BisTris was prepared by adding 62.70 g. of BisTris to HPLC grade distilled water to a final volume of about 180 ml. After stirring, the pH was adjusted to 7.30 with concentrated $HNO_3$. The resulting volume was adjusted to the mark with distilled water. Similarly a 200 ml solution of 2.0 M BisTris was prepared by using 83.60 g. of BisTris. The pH was adjusted to pH 7.60 before adjusting the volume. Both BisTris solutions were stirred for 10 min. at room temperature and filtered to remove any visible particles.

A diluted enzyme reagent was prepared by adding 5 ml of ALAD containing 3.1 U/mg to 35 ml of 250 mM BisTris. The 250 mM BisTris diluent solution was prepared by adding 5.23 g. BisTris to 100 ml of HPLC grade distilled water and stirring. DTT was added to 10 mM in the diluted enzyme reagent. Other sulfhydryl compounds such glutathione, mercaptoethanol and cysteine can be used as a reducing agent instead of DTT. The pH of the diluent solution was adjusted to pH 7.0 by adding 50% NaOH. The diluted enzyme reagent was stored at 2°–8° C. under nitrogen gas.

A 25 mM ALA and 10 uM $ZnCl_2$ substrate solution was prepared by adding 0.210 g. ALA, 25 ul 20 mM $ZnCl_2$ and 50 ml HPLC distilled water to a flask. After stirring, the substrate solution was stored at 2.8° C. in the dark.

A stop reagent containing 10% TCA was prepared by adding 20.000 g of TCA, 0.1 M $HgCl_2$ and HPLC grade distilled water to 200 ml. The solution was stirred and filtered at 0.80 um.

A pretreatment reagent containing 17.5 % TCA was prepared by adding 17.5 g TCA to 100 ml HPLC distilled water and stirring.

A modified Ehrlich's Reagent was prepared by adding 12.5 g DMAB, 250 ml glacial acetic acid and 122.5 ml of 60% perchloric acid and mixing. The final volume was adjusted to 500 ml by adding more glacial acetic acid. The modified Ehrlich's Reagent was stored in the dark at 2°–8° C.

A whole blood mixture was prepared by collecting 180 ml of whole blood from type B+ and O+ donors and adding 20 mg of sodium heparin. A test sample containing 40 ug/dl $Pb^{+2}$ was prepared by adding 0.320 g of 10 mg/dl $Pb^{+2}$ to 80.0 ml of the whole blood mixture. The remainder of the whole blood mixture was used as a control containing 0 ug/dl of $Pb^{+2}$. After vigorous mixing, both test samples were stored for 4 hours with mixing every 30 min., and subsequently, overnight at 2°–8° C.

For each enhancer, a neutralizing solution containing 0.5 M enhancer and 1.5 M BisTris was prepared by adding 7.5 ml of the 2 M Bis-Tris solution to following amounts of enhancers Na Citrate 1.470 gm; IDA 0.975 g; NTA 1.175 g; EGTA 1.900 g; Histidine 1.050 g; HEIDA 0.885 g; MIDA 0.735 g; BenzylIDA 1.115 g; HQSA 1.125 g; EDTA 1.840 g; EDTA 1.840 g; and PEN 0.745 g. After stirring, HPLC grade distilled water was added to each neutralizing solution to obtain a final volume of about 9.5 ml. Subsequently, the enhancer solutions were vigorously stirred overnight. The neutralizing solutions containing Histidine, HQSA and PEN enhancer reagents were heated to about 70° C. to complete dissolution and then cooled to room temperature. The pH of each neutralizing solution was then adjusted to pH 7.25 with either concentrated $HNO_3$ or 50% NaOH.

Whole blood samples containing 0 ug/dl and 40 ug/dl $Pb^{+2}$ were dispensed in 24.5 ml amounts and were pretreated with 10.5 ml of the TCA pretreatment solution. Each sample was centrifuged for five minutes and the supernatants were saved. From each supernatant solution 180 ul was mixed by vortex with 180 ul of neutralizing buffer. From this neutralized supernatant solution 100 ul was added to 100 ul of the dilute enzyme reagent and mixed by vortex and incubated for 15 min in a 37° C. water bath.

Subsequently 100 ul of the substrate solution was added, mixed by vortex and incubated for 30 min. in the water bath. The stop reagent was added in an amount of 250 ul and mixed by vortex. The mixture was centrifuged for two minutes to remove insoluble DTT.

The supernatant mixture was removed and added to 500 ul of the modified Ehrlich's reagent. After mixing by vortex and incubating for 10 min. at room temperature, the absorbance was recorded at 555 nm.

Results

The absorbance data for each enhancer was collected at the following concentrations, measured in mM after being mixed with the pretreated whole blood supernatant:0.25, 1.00, 2.50, 10.00, 25.00, 100.00 and 250.00. Table 1 shows the measured absorbance span for each enhancer in the samples containing 0 ug/dl and 40 ug/dl $Pb^{+2}$. The equilibrium constant of $Pb^{+2}$ for each enhancer as reported in either Bjerrum, supra, or Sillen, supra, is included in Table 1.

TABLE 1

| Enhancer | Conc. mM | Absorbance Span | Pb$^{+2}$ Equilibrium Constant log (Km) |
| --- | --- | --- | --- |
| Control | — | 0.006 | — |
| Na Citrate | 250.00 | 0.106 | 4.3 |
| Histidine | 250.00 | 0.915 | 6.4 |
| IDA | 250.00 | 0.801 | 7.5 |
| MIDA | 100.00 | 0.735 | 8.0 |
| HQSA | 2.50 | 0.891 | 8.5 |
| HEIDA | 250.00 | 0.223 | 9.5 |
| NTA | 10.00 | 0.110 | 11.6 |
| Penicillamine | 100.00 | 0.311 | 13.0 |
| EGTA | 10.00 | 0.016 | 14.7 |

As a matter of convenience, the reagents can be provided as kits, where the reagents are in predetermined ratios, so as to substantially optimize the sensitivity of assay in the range of interest. Wet or dry reagents may be used. After reconstitution of dry reagents, in predetermined volumes, the concentration of the reagents will be at appropriate levels.

The reagents may be mixed with various ancillary materials such as neutralizing solutions, buffers, substrate solutions, and the like. The method of the present invention is performed by combining certain of the three reagents in a mixture essential for the pretreatment of the lead sample. One is the acidified lead sample, the second is the neutralizing reagent and the third is the enhancer. The enhancer may be kept separate or added to either the neutralizing solution or the acidified lead sample.

As demonstrated above, the present invention provides chelating reagents to enhance the sensitivity and accuracy of a lead assay using the ALAD enzyme. More of the lead in the sample is recovered and detected as compared to using the assay in the absence of the enhancer.

Although the invention has been described using a photometric analysis of the PBG to determine lead contamination, the present invention is not so limited. The method and compositions of the present invention can be employed in various heterogeneous and homogeneous immunoassay system formats known in the art. Such immunoassay system formats include, but are not intended to be limited to, competitive, sandwich and immunometric techniques. Generally, such immunoassay systems depend upon the ability of a binding member, such as, for example, an immunoglobulin (i.e., a whole antibody or fragment thereof) to bind to a specific analyte from a test sample, wherein a labeled reagent comprising a binding member labeled with a signal generating compound such as a fluorescent or chemiluminescent molecule is employed to determine the extent of binding. Typically, the extent of binding in such immunoassay system formats is determined by the amount of the signal generating compound present in the labeled reagent which either has or has not participated in a binding reaction with the analyte, wherein the signal which is generated by the signal generating compound as described herein is detected and correlated to the amount of analyte present in the test sample. Accordingly, the amount of analyte is correlated to the level of lead contamination of the test sample.

Homogeneous immunoassays typically are performed in a competitive immunoassay format involving a competition between an analyte from a test sample and a labeled reagent for a limited number of receptor binding sites on an antibody to the analyte. The labeled reagent comprises the analyte or analyte-analog labeled with a signal generating compound wherein the concentration of analyte in the test sample determines the amount of the labeled reagent that will specifically bind to the antibody. The amount of the labeled reagent-antibody conjugate produced by such binding may be quantitatively measured and is inversely proportional to the amount of analyte present in the test sample.

Heterogeneous immunoassay formats involve a labeled reagent or tracer comprising an analyte, analyte-analog, or an antibody thereto, labeled with a signal generating compound, to form a free species and a bound species. In order to correlate the amount of tracer in one of such species to the amount of analyte present in the test sample, the free species must first be separated from the bound species, which can be accomplished according to methods known in the art employing solid phase materials for the direct immobilization of one of the binding participants in the binding reaction, such as the antibody, analyte-analog, or analyte, wherein one of the binding participants is immobilized on a solid phase material, such as a test tube, beads, particles, microparticles or the matrix of fibrous material, and the like, according to methods known in the art. The solid phase materials can be any solid material to which a binding participant can be immobilized and include, but are not intended to be limited to, beads, magnetic particles, paramagnetic particles, microparticles or macro particles, test tubes, and microtiter plates. Such solid phase materials can be made from synthetic materials, naturally occurring materials, or naturally occurring materials which have been synthetically modified, and include, but are not intended to be limited to, cellulose materials, such as paper, cellulose and cellulose derivatives such as cellulose acetate and nitrocellulose; fiberglass; naturally occurring cloth such as cotton; synthetic cloth such as nylon; porous gels, such as silica, agarose, dextran, and gelatin; porous fibrous matrixes; starch based materials, such as cross-linked dextran chains; ceramic materials; olefin or thermoplastic materials including polyvinyl chloride, polyethylene, polyvinyl acetate, polyamide, polycarbonate, polystyrene, copolymers of vinyl acetate and vinyl chloride, combinations of polyvinyl chloride-silica; and the like.

Heterogeneous immunoassays can be performed in a competitive immunoassay format wherein, for example, the antibody can be immobilized to a solid phase material whereby upon separation, the signal generated by the signal generating compound of the bound or free species can be detected and correlated to the amount of analyte present in the test sample. Another form of a heterogeneous immunoassay employing a solid phase material is referred to as a sandwich immunoassay, which involves contacting a test sample containing, for example, an antigen with a protein such as an antibody or another substance capable of binding the antigen, and which is immobilized on a solid phase material. The solid phase material typically is treated with a second antigen or antibody which has been labeled with a signal generating compound. The second antigen or antibody then becomes bound to the corresponding antigen or antibody on the solid phase material and the signal generated by the signal generating compound in the bound or the free species can be detected and correlated to the amount of analyte present in the test sample.

The present invention is also not limited to the analysis of lead contamination in a blood sample. The test sample can be derived from any biological source, such as a physiological fluid, including, blood, saliva, ocular lens fluid, cerebral spinal fluid, sweat, urine, milk, ascites fluid, raucous, synovial fluid, peritoneal fluid, amniotic fluid or the like. The test sample can be pretreated prior to use, such as preparing plasma from blood, diluting viscous fluids, or the like;

methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the lead. Generally, any sample suspected of containing lead can be analyzed as long as the lead is liberated from the physical or chemical mixture in which it is presented to produce elemental lead.

While particular embodiments and applications of the present invention have been illustrated and described, it is to be understood that the invention is not limited to the precise construction and compositions disclosed herein and that various modifications, changes, and variations which will be apparent to those skilled in the art may be made in the arrangement, operation, and details of construction of the invention disclosed herein without departing from the spirit and scope of the invention as defined in the appended claims.

What is claimed is:

1. A lead assay comprising the steps of:
  (a) providing an aqueous solution suspected of containing lead;
  (b) isolating said lead from said solution in such a manner that said lead remains in solution:
  (c) introducing to said solution of step (b) an enhancing reagent that combines with said lead and prevents said lead from precipitating from said solution; followed by
  (d) introducing to said solution an enzyme the activity of which is inhibited in the presence of lead and a substrate for said enzyme: and
  (e) measuring the amount of lead as a function of said activity of said enzyme.

2. The lead assay of claim 1 wherein the reagent which combines with lead in step (b) comprises a chelator having a lead equilibrium binding constant in the range of about 4 log K to aout 13 log K.

3. The lead assay of claim 2 wherein the lead equilibrium binding constant is in the range of about 6 log K to about 9 log K.

4. The lead assay of claim 2 wherein the chelator is selected from the group consisting of N-benzyliminodiacetic acid, ethylenebis(oxyethylenenitrilo) tetraacetic acid, ethylenediaminetetraacetic acid, L-histidine monohydrochloride monohydrate, N-(2-hydroxyethyl)-iminodiacetic acid, iminodiacetic acid, DL-penicillamine, methyliminodiacetic acid, nitrilotriacetic acid, sodium citrate, and d-hydroxyquinoline-5-sulfonic acid hydrate.

5. A lead assay comprising the steps of:
  (a) providing an aqueous solution suspected of containing lead, said solution having been separated from compounds that are affected by the presence of lead, said solution further having been neutralized;
  (b) introducing into said solution a lead chelator having a lead equilibrium binding constant in the range of about 4 log K to about 13 log K; followed by
  (c) introducing into said solution (i) an enzyme the activity of which is inhibited by lead and (ii) a substrate which reacts with the enzyme;
  (d) incubating the solution of step (c):
  (e) stopping the incubation step after a predetermined interval; and
  (f) measuring the amount of lead as a function of enzyme activity.

6. The lead assay of claim 5 wherein the isolating step includes releasing lead from a sample of whole blood.

7. The lead assay of claim 5 wherein the method further includes neutralizing the sample solution before the enzyme incubating step.

8. The lead assay of claim 5 wherein the chelator has a lead equilibrium binding constant in the range of about 6 log K to about 9 log K.

9. The method of claim 5 wherein the chelator is selected from the group consisting of N-benzyliminodiacetic acid, ethylenebis(oxyethylenenitrilo) tetraacetic acid, ethylenediaminetetraacetic acid, L-histidine monohydrochloride monohydrate, N-(2-hydroxyethyl)-iminodiacetic acid, iminodiacetic acid, DL-penicillamine, methyliminodiacetic acid, nitrilotriacetic acid, sodium citrate, and d-hydroxyquinoline-5-sulfonic acid hydrate.

10. The method of claim 5 wherein the chelator is selected from the group consisting of 8-hydroxy-5-(2'-hydroxyphenylazo)quinoline, 8-hydroxy-5-(phenylazo) quinoline, N-(2-carboxyphenyl)iminodiacetic acid, N-(acetonyl)iminodiacetic acid, N-(dithiocarboxy) aminoacetic acid, N,N-bis(2'-hydroxyethyl)glycine, and glycine.

11. The method of claim 5 wherein the chelator is selected from the group consisting of dihydroxyphenyl acetic acid, N-(2'-carboxyethyl) iminodiacetic acid, dihydroxybenzoic acid, 3,4,dihydroxybenzene sulfonic acid, melonic acid, 1-hydroxy-1-(3'-pyridyl) methane sulfonic acid, and 4-aminopyridine-2,6-dicarboxylic acid.

12. The lead assay of claim 5 wherein the aqueous solution in step (b) is acidified and the lead chelator of step (c) is present in a neutralizing buffer such that performing step (c) results in bringing the acidified solution of step (b) to neutral pH.

13. The lead assay of claim 5 wherein the enzyme is aminolevulinic acid dehydratase.

14. The lead assay of claim 13 wherein the enzyme is activated with a reducing agent selected from the group consisting of dithiothreitol, glutathione, mercaptoethanol and cysteine.

15. The lead assay of claim 5 wherein the enzyme incubating step includes first incubating the sample solution in the presence of aminolevulinic acid dehydratase and subsequently incubating the sample solution in the presence of the substrate.

16. The lead assay of claim 15 wherein the substrate includes aminolevulinic acid.

17. The lead assay of claim 5 wherein the stopping step includes adding a stop reagent.

18. The lead assay of claim 17 wherein the stop reagent includes $HgCl_2$.

19. The lead assay of claim 5 wherein step (d) includes incubating the sample solution in the presence of a coloring reagent.

20. The lead assay of claim 19 wherein the coloring reagent is selected from the group consisting essentially of dimethylaminobenzaldehyde and dimethylaminocinnamaldehyde.

21. An aqueous lead assay reagent solution consisting essentially of neutralizing buffer and a lead chelator having a lead binding constant in the range of about 4 log K to about 13 log K wherein the concentration of the chelator in the solution is in the range of 0.5 mM to 500 mM.

22. The reagent solution of claim 21 wherein the chelator has a lead equilibrium binding constant in the range of about 6 log K to about 9 log K.

23. The reagent solution of claim 21 wherein the chelator is selected from the group consisting of N-benzyiminodiacetic acid, ethylenebis(oxyethylenenitrilo)tetraacetic acid, ethylenediaminetetraacetic acid, L-histidine monohydrochloride monohydrate, N-(2-hydroxyethyl)-iminodiacetic acid, iminodiacetic acid, DL-penicillamine, methyliminodiacetic acid, nitrilotriacetic acid, sodium citrate, and d-hydroxyquinoline-5-sulfonic acid hydrate.

24. The reagent solution of claim 23 wherein the chelator is selected from the group consisting of 8-hydroxy-5-(2'-hydroxyphenylazo)quinoline, 8-hydroxy-5-(phenylazo)quinoline, N-(2-carboxyphenyl)iminodiacetic acid, N-(acetonyl) iminodiacetic acid, N-(dithiocarboxy) aminoacetic acid, N,N-bis(2'-hydroxyethyl)glycine, and glycine.

25. The reagent solution of claim 21 wherein the chelator is selected from the group consisting of dihydroxyphenyl acetic acid, N-(2'-carboxyethyl) iminodiacetic acid, dihydroxybenzoic acid, 3,4,dihydroxybenzene sulfonic acid, melonic acid, 1-hydroxy-1-(3'-pyridyl)methane sulfonic acid, and 4-aminopyridine-2,6-dicarboxylic acid.

26. A lead assay reagent kit comprising:
   a container having a reagent solution consisting essentially of an aqueous neutralizing buffer and present therein a reagent which is capable of forming a compound or complex with lead such that adding the solution to an acidified aqueous sample containing lead will neutralize the aqueous sample while preventing precipitation of lead therefrom;
   a container comprising an enzyme which is inhibited in the presence of lead; and
   a container comprising a substrate which reacts with said enzyme.

27. The lead assay reagent kit of claim 26 wherein the kit further includes:
   a container for a stop reagent for stopping the reaction between the substrate and the enzyme;
   a container for a coloring reagent for forming a chromophore upon reaction with a product of the substrate and enzyme reaction; and;
   a reducing reagent included in either the substrate or enzyme containiner in an amount effective to increase the activity of the enzyme reacting with the substrate.

28. The lead assay reagent kit of claim 27 wherein the reducing agent comprises dithiothreitol, the enzyme comprises aminolevulinic acid dehydratase and the substrate comprises aminolevulinic acid and the product of the substrate and enzyme comprises porphobilinogen.

* * * * *